United States Patent [19]

Stewart et al.

[11] Patent Number: 4,510,060

[45] Date of Patent: Apr. 9, 1985

[54] MEASUREMENT OF BS&W IN CRUDE OIL STREAMS

[75] Inventors: Thomas L. Stewart, Houston; Florian C. Demny, Pasadena, both of Tex.

[73] Assignee: Shell Oil Company, Houston, Tex.

[21] Appl. No.: 291,597

[22] Filed: Aug. 10, 1981

[51] Int. Cl.³ .............................................. B01D 37/00
[52] U.S. Cl. .................................... 210/746; 73/61 R; 73/61.1 R; 134/5; 134/22.11; 134/40; 210/774; 210/781; 210/149
[58] Field of Search ............... 210/636, 742, 746, 773, 210/774, 781, 149; 134/5, 22.1, 22.11, 23, 40, 166 C; 73/61 A, 61.1 A

[56] References Cited

U.S. PATENT DOCUMENTS

| | | |
|---|---|---|
| 2,958,223 | 11/1960 | Hubby . |
| 3,189,180 | 6/1965 | Scott et al. . |
| 3,192,764 | 7/1965 | Jasek . |
| 3,546,926 | 12/1970 | Dunanent et al. ................... 73/61.1 |
| 3,638,476 | 2/1972 | Patterson et al. . |
| 3,652,319 | 3/1972 | Amidon et al. ..................... 134/5 X |
| 3,796,318 | 3/1974 | Underwood .................... 210/746 X |
| 3,874,399 | 4/1975 | Ishihara .............................. 134/5 X |
| 4,055,986 | 11/1977 | Stewart et al. . |
| 4,184,952 | 1/1980 | Stewart .............................. 210/781 |
| 4,210,015 | 7/1980 | Euzen et al. . |

Primary Examiner—John Adee

[57] ABSTRACT

Temperature variations of fluid streams within a BS&W recorder system are controlled by heat exchange and recycling through the pump to reduce waxing and capacitance measurement errors.

5 Claims, 1 Drawing Figure

MEASUREMENT OF BS&W IN CRUDE OIL STREAMS

BACKGROUND OF THE INVENTION

A device for measurement of basic sediment and water (BS&W) in a predominantly non-aqueous stream (e.g. pipeline crude oil) is disclosed in U.S. Pat. No. 4,184,952. This device is an improvement on capacitance type instruments of the art which are dependent upon the extent to which the intrinsic dielectric constant of the subject fluid varies with time. The gravity and physical composition of crude oil are two factors which determine its intrinsic dielectric constant. If one or both of these properties should vary, instruments measure the accompanying change in the dielectric constant as percent BS&W. This yields an inaccurate measurement of BS&W because instruments must be initially set to read zero BS&W at the intrinsic dielectric constant of the fluid. The capacitance type instruments of the prior art have no means for automatically correcting the zero BS&W setting to compensate for periodic variations in the oil properties mentioned. By comparison, the device of U.S. Pat. No. 4,184,952 provides for automatic compensation of BS&W measurements by producing a clean, dry sample of the line fluid for measurement of its intrinsic dielectric constant. In this way, the true BS&W content of the fluid is measured by finding the difference between the dielectric constants of the wet and dry streams.

Even though the improvement over the prior art represented by the invention of U.S. Pat. No. 4,184,952 is substantial, it now has been discovered that other improvements can be made which even further improve the efficiency and accuracy of this invention. Thus, temperature variations within the apparatus of the invention can cause some loss of accuracy of readings. For example, the indications from the wet and dry cells of the apparatus are compared to determine BS&W content. This comparison presumes that all other properties of the oils are identical, including temperature. The error introduced by temperature difference is about 0.02% BS&W per degree Fahrenheit. While this error might be neglected if the temperature difference were only one or two degrees, it is desirable to reduce error introduced by a larger temperature difference, for example up to 18° F. temperature difference between the wet and dry cells as have been noted with the apparatus of U.S. Pat. No. 4,184,952.

In addition, changing temperatures within the apparatus of U.S. Pat. No. 4,184,952 tend to cause wax to plate the inner surfaces of the various parts thereof. This will usually occur when the stream leaving the pipeline is cool enough to contain traces of solidified wax. Passage through the pump of the apparatus, centrifugal filter and associating tubing tends to raise the temperature of the oil and melt some of the crystals. The melted wax will then re-solidify on any surfaces that are cooler than the oil. This occurs, for example in a heat exchanger, to be described hereinafter, wherein the warm, dry oil leaving the centrifuge is cooled by the incoming wet stream from the pipeline. In this case, the wax is detrimental in two ways: (1) it tends to impede flow and (2) it reduces the heat exchange capacity of the affected surfaces. It also has been observed that a certain amount of residue tends to collect in the dry oil capacitance measurement cell. The cell comprises two coaxial tubes electrically insulated from each other within the annular space between the tubes, which constitutes an electrical capacitor whose value depends upon the material in the annular space. The residue buildup usually tends to cause an error in the direction of wetness. Thus, the dry cell indicates less dry than it should compared to the wet cell, where flow is more rapid and the residue does not tend to accumulate.

Accordingly, the present invention is directed to overcoming the above and other problems described hereinafter by means of the following disclosed improvements.

SUMMARY OF THE INVENTION

Figure 1:
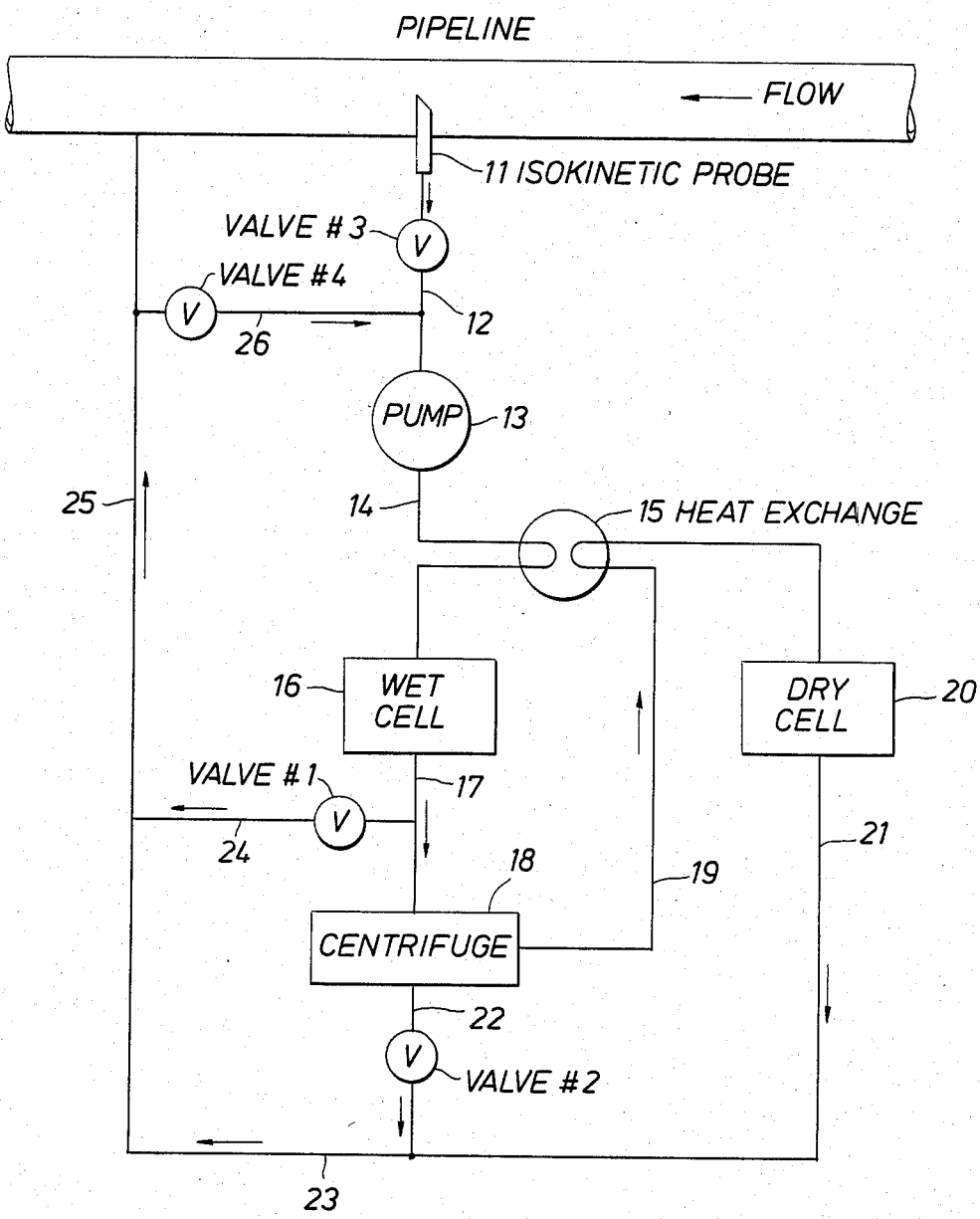
FIG. 1 provides a schematic diagram of oil flow within a BS&W measurement system of the present invention.

It is an object of the present invention to alleviate or overcome difficulties arising from temperature variations within the BS&W measurement system of the present invention.

Accordingly, the present invention provides a process for measuring the water content of a wet stream which is predominantly non-aqueous by removing a sample of the wet stream, extracting a dry stream sample from the wet stream sample, heat exchanging the dry stream sample with the wet stream sample to reduce any temperature therebetween, and measuring the dielectric constants of the wet stream sample and the dry stream sample to facilitate determining the water content of the wet stream.

Preferably, the wet stream is pipeline crude oil containing water and sediment and having a varying dielectric constant, and the wet stream sample is admitted to an outer chamber containing an inner chamber having a wall formed of a filter, the inner chamber is rotated while pressuring the wet stream sample from the outer chamber into the inner chamber, and sediment is filtered from the wet stream sample passing into the inner chamber and centrifugal force in the inner chamber forces water in the wet stream sample back into the outer chamber, so that clean, dry sample is withdrawn from the inner chamber.

In addition, the present invention provides a process for de-waxing the inner surfaces of apparatus receiving waxy oil via pump at temperatures whereat waxy components of the oil deposit on contacting surfaces therewithin, by increasing the temperature of the waxy oil by recycling the oil through the pump until the oil is at a temperature sufficient to dissolve the waxy deposits. Preferably, the waxy oil contains water and the apparatus is an instrument for measuring the amount of water in the waxy oil. Even more preferably, the instrument is employed to extract a dry stream from the wet, waxy oil stream and measure the difference between the dielectric constants of the wet and dry streams to facilitate determining the true water content of the waxy oil.

Generally, the present invention provides a process for increasing the temperature of a stream to a desired range, said stream being delivered by pump from a source to a station and then at least partially returned to the source, by at least temporarily recycling through the pump the part of the stream to be returned to the source until sufficient energy is imparted from the pump to increase the temperature of the stream to the desired range.

DESCRIPTION OF PREFERRED EMBODIMENTS

FIG. 1 of the drawings discloses a pipeline containing crude oil or another predominantly non-aqueous fluid. A wet stream sample is withdrawn from the pipeline by means of an isokinetic probe 11 or other means known to the art. The sample is passed via line 12 through valve 3 and into a pump 13, preferably of the variable rate type. From there a stream 14 passes through a heat exchanger 15 and then into a wet cell 16 which is preferably a capacitor having coaxial tubes which measure the capacitance of the fluid between the tubes in the wet state. From there, a stream 17 passes into a centrifuge 18, substantially as described in U.S. Pat. No. 4,184,952. A clean, dry stream 19 is withdrawn from the centrifuge and passed through heat exchanger 15 and into dry cell 20. From dry cell 20 a stream 21 is merged with stream 22 which passes through valve 2 to form stream 23 which is returned along with stream 24, which passes through valve 1 back to the pipeline via stream 25.

In order to raise the temperature of the system and dissolve any deposited wax therein, the heating method of this invention requires closing valve 3 and opening valve 4 whereby stream 25 then passes via line 26 back through pump 13. Thus, the process utilizes the energy of the circulation pump to create heat via the friction in the system. This valving operation causes the stream to circle back on itself while addition of new oil is stopped. The result is a quick increase in temperature of 50° F. or more in a few minutes which melts wax deposits. This dewaxing cycle may be necessary, more or less, once each day, or once each 8-hour shift during winter months. A timer and solenoid valve (not shown) may be designed into the system to accomplish the dewaxing cycle automatically.

Heat exchanger 15 is employed to accomplish temperature equalization within the system to offset any discrepancies between capacitance readings between wet cell 16 and dry cell 20. It is not unusual to have a difference of temperature of as much as 18° F. without the existence of heat exchanger 15. Accordingly, the warm stream 19 leaving the centrifuge 18 and proceeding to the dry cell 20 first gives up heat to the incoming stream 14. Since the volumetric ratio of the streams is for example about 30 and ranges from 5 to 100 or more, the temperature of the incoming stream is hardly affected as the dry stream temperature is dropped to within a degree or so of the wet stream temperature. A manual bypass around the heat exchanger (not shown) permits determination of a temperature error factor. Bypassing the heat exchanger raises the dry stream temperature, whereupon the ratio change of BS&W variation to temperature change can be determined.

What is claimed is:

1. A process for measuring the water content of a wet stream which is predominantly non-aqueous, comprising, removing a sample of the wet stream, extracting a dry stream sample from the wet stream sample, heat exchanging the dry stream sample with the wet stream sample to reduce any temperature difference therebetween, and measuring the dielectric constants of the wet stream sample and the dry stream sample to facilitate determining the water content of the wet stream.

2. The process of claim 1 wherein the volumetric ratio of the wet stream sample to dry stream sample ranges from about 5 to about 100 or more.

3. The process of claim 1 wherein the wet stream is pipeline crude oil containing water and sediment and having a varying dielectric constant, the wet stream sample is admitted to an outer chamber containing an inner chamber having a wall formed of a filter, the inner chamber is rotated while pressuring the wet stream sample from the outer chamber into the inner chamber, sediment is filtered from the wet stream sample passing into the inner chamber and centrifugal force in the inner chamber forces water in the wet stream sample back into the outer chamber, and clean dry sample is withdrawn from the inner chamber.

4. Apparatus for measuring the water content of a wet stream which is predominantly non-aqueous, comprising, means for removing a sample of the wet stream, means for extracting a dry stream sample from the wet stream sample, a heat exchanger for reducing any temperature difference between the dry stream sample and the wet stream sample, and means for measuring the dielectric constants of the wet stream sample and the dry stream sample.

5. The apparatus of claim 4 wherein the wet stream is crude oil containing BS&W and the extracting means is part of an instrument for measuring the BS&W.

* * * * *